United States Patent [19]

Schauss et al.

[11] Patent Number: 6,063,026

[45] Date of Patent: May 16, 2000

[54] MEDICAL DIAGNOSTIC ANALYSIS SYSTEM

[75] Inventors: Mark A. Schauss, Incline Village, Nev.; Patricia Kane, Millville, N.J.

[73] Assignee: Carbon Based Corporation, Incline Village, Nev.

[21] Appl. No.: 08/620,385

[22] Filed: Mar. 22, 1996

Related U.S. Application Data

[63] Continuation-in-part of application No. 08/568,752, Dec. 7, 1995, Pat. No. 5,746,204.

[51] Int. Cl.$^7$ ........................................................ A61B 5/00
[52] U.S. Cl. ............................................. 600/300; 128/923
[58] Field of Search .................................. 128/630, 920, 128/921, 923, 924, 898, 670; 600/300

[56] References Cited

U.S. PATENT DOCUMENTS

| | | |
|---|---|---|
| 4,290,114 | 9/1981 | Sinay . |
| 4,731,725 | 3/1988 | Suto et al. . |
| 4,733,354 | 3/1988 | Potter et al. . |
| 5,023,785 | 6/1991 | Adrion et al. . |
| 5,199,439 | 4/1993 | Zimmerman et al. . |
| 5,255,187 | 10/1993 | Sorensen . |
| 5,404,292 | 4/1995 | Hendrickson . |
| 5,437,278 | 8/1995 | Wilk . |
| 5,463,548 | 10/1995 | Asada et al. . |
| 5,551,436 | 9/1996 | Yago ........................................ 128/670 |
| 5,594,638 | 1/1997 | Lliff . |
| 5,618,729 | 4/1997 | Izraelevitz et al. ................... 435/288.7 |
| 5,642,731 | 7/1997 | Kehr ........................................ 128/630 |

OTHER PUBLICATIONS

Brief filed Mar., 1998 in Civil Action, *Kane et al. vs. Carbon Based Corporation*, No. CUM–L001368–97(S.P. Ct. NS,Cumberland County).

Certification of Kent Myles filed Mar., 1998 in Civil Action, *Kane et al. vs Carbon Based Corporation*,No. CUM–L001368–97(S.P. Ct. NS, Cumberland County)(Exhibit A from Brief (AW)).

Certificationof Timothy Cunninghamm filed Mar., 1998 in Civil Action, *Kane et al. vs. Carbon Based Corporation*,No. CUM–L001368–97 (S.P. Ct. NS, Cumberland County)(Exhibit A from Brief (AW)).

Supplemental Certification of Edward Kane filed Mar., 1998 in Civil Action, *Kane et al. vs. Carbon Based Corporation*, No. CUM–L001368–97 (S.P. Ct. NS, Cumberland County).

Lendon H. Smith, *Feed Your Body Right*, pp. 114–171, 184–189, 1994, M.Evans and Company, Inc., New York (Exhibit A from Supplemental Certification of Edward Kane (AZ).

Supplemental Certification of Patricia Kane filed Mar., 1998 in Civil Action, *Kane et al. vs. Carbon Based Corporation*, No. CUM–L001368–97 (S.P. Ct. NS, Cumberland County).

(List continued on next page.)

*Primary Examiner*—Samuel G. Gilbert
*Attorney, Agent, or Firm*—Robert O. Guillot

[57] ABSTRACT

The present invention is a computerized medical diagnostic method. It includes a first database containing a correlation of a plurality of diseases with a plurality of indicators associated with each such disease. A second database includes human experience test results associated with each indicator. An individual's test results are then compared with the second database data to determine presence levels for each indicator. Thereafter the presence levels are compared with the data in the first database to provide a pattern matching determination of diseases associated with the various indicator presence levels.

The presence level indicators for an individual may be affected by many environmental and/or personal factors such as age, sex, race, pregnancy, residence location, previous or current diseases, previous or current drug usage, etc., all of which are factors to be considered in creating an accurate analysis system. The present invention provides a method for correlating such factors with the various test indicators to identify therapeutic and/or contraindicated treatments and drugs.

38 Claims, 9 Drawing Sheets

OTHER PUBLICATIONS

Fischbach et al., *Manual of Laboratory and diagnostic Tests*, pp. I–III,4–22,4–23,276,277,1992 J.B.Lippincott Company, Pennsylvania.

Young, Donald S., *Effects of Drugs on Clinical Laboratory Tests*, pp. I,3–236,3–237,1995, AACC Press, Fourth Edition, Washington D.C.

Young, Donald S., *Effects of Preanalytical Variables on Clinical Laboratory Tests*, pp. I, II, 4–472, 4–473, 1996, AACC Press, Second Edition, Washing D.C.

Health Equations, Blood Test Evaluation of Patricia Kenney on Mar. 23, 1995 (2 pages).

Blood Test Evaluation Copyright 1988 by Life Balances, Inc. (2 pages).

Friedman, Richard B. et al.,*Effects of Disease on Clinical Laboratory Tests*, p. 4–111, .1989, AACC Press, Washingon D.C.

Young, Donald S.,*Effects of Preanalytical Variables on Clinical Laboratory Tests*, pp. 3–287,1993,AACCPRESS, First Edition, Washing D.C.

Young, Donald S., *Effects of Drugs on Clinical Laboratory Tests*, pp. 4–57,1995, AACC Press, Fourth Edition, Washington D.C.

MEDICAL DIAGNOSTIC ANALYSIS SYSTEM

This application is a continuation-in-part of application Ser. No. 08/568,752 filed on Dec. 7, 1995 now U.S. Pat. No. 5,746,204.

BACKGROUND OF THE INVENTION

1. Field of the Invention

The present invention relates generally to automated medical diagnosis systems, and more particularly to such systems which compare patient diagnostic data with predetermined ranges of specific indicators to provide a specific disease diagnosis and suggested or contraindicated treatment strategies.

2. Description of the Prior Art

Medical research in the second half of the 20th century has produced, and continues to produce, an ever increasing body of knowledge. The complexity and interrelationships of various diseases and the indicators that may be detected in various diagnostic tests for the diseases are more than sufficient to tax the capacity of most medical practitioners. To aid medical practitioners in disease diagnosis, computerized expert systems have been, and are being developed to collate medical diagnostic data with various diseases to guide physicians in prescribing treatments for their patients. Such prior art medical diagnostic systems do not adequately provide an analytical framework for analyzing the individual patient's diagnostic results to collate such results into a disease indicator pattern. Furthermore, such systems do not address therapeutic and/or contraindicated treatment strategies.

SUMMARY OF THE INVENTION

The present invention is a computerized medical diagnostic method. It includes a first database containing a correlation of a plurality of diseases with a plurality of indicators associated with each such disease. A second database includes human experience test results associated with each indicator. An individual's test results are then compared with the second database data to determine presence levels for each indicator. Thereafter the presence levels are compared with the data in the first database to provide a determination of disease pattern matches associated with the various indicator presence level.

The presence level indicators for an individual may be affected by many environmental and/or personal factors such as age, sex, race, pregnancy, residence location, previous or current diseases, previous or current drug usage, etc., all of which are factors to be considered in creating an accurate analysis system. The present invention provides a method for correlating such factors with the various test indicators to identify therapeutic and/or contraindicated treatments and drugs.

It is an advantage of the present invention that it provides a method for automated analysis of an individual's test results to provide increased accuracy in disease identification.

It is another advantage of the present invention that it provides increased accuracy in automated disease identification systems by determining indicator presence levels for use in the disease identification analysis.

It is a further advantage of the present invention that it provides an automated medical diagnostic database system wherein indicator test results for specific individuals are automatically categorized as increased, normal or decreased for increased accuracy in disease determination.

It is yet another advantage of the present invention that it provides an automated medical diagnostic database system wherein indicator test results are combined in various panels to provide diagnostic information regarding various bodily conditions and functions.

It is yet a further advantage of the present invention that it provides an automated medical diagnostic database system wherein diagnostic data from a first date and a second date can be compared to provide information regarding the change in an individual's medical health and the effectiveness of an ongoing medical treatment program.

It is still another advantage of the present invention that it provides an automated medical diagnostic database system wherein the known effects of various drugs and other nutritional-biochemical elements can be utilized to better analyze an individual's health status, and to identify therapeutic and/or contraindicated drugs and elements.

It is still a further advantage of the present invention that it provides an automated medical diagnostic database system wherein the effects of personal and/or environmental factors such as age, sex, pregnancy, residence location, prior or current diseases and drug usage, may be utilized to provide a more accurate medical health analysis.

These and other features and advantages of the present invention will become well understood upon reading the following detailed description of the invention.

IN THE DRAWINGS

DETAILED DESCRIPTION OF THE PREFERRED EMBODIMENTS

Generally, the basic system of the present invention involves the comparison of test results, typically from blood or other bodily fluids of an individual with known indicators for various diseases to determine the likelihood that an individual might have particular ones of the diseases. The method is basically accomplished in six steps which are depicted in FIG. 1 and described herebelow.

Figure 1:
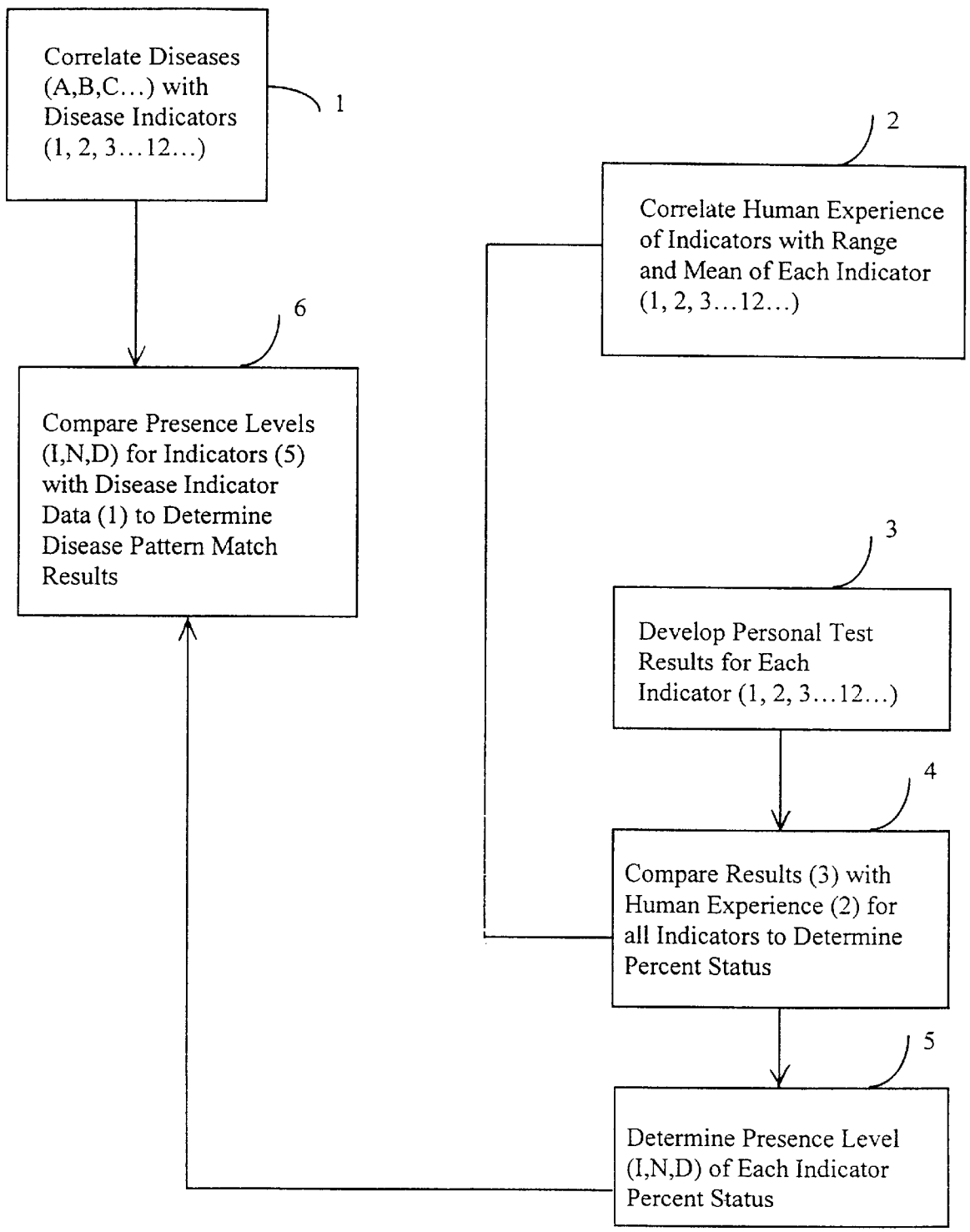
FIG. 1 is a block diagram of the basic disease pattern matching analytical method of the present invention.

FIG. 1 is a schematic diagram setting forth the various steps in the analytical disease indication method of the present invention. As depicted therein, step 1 is the creation of a database for utilization within a computer diagnostic system. The database is a correlation of various diseases, denoted generally as A, B, C . . . , with levels (Increased, Normal, Decreased) of various specific indicators, denoted generally as 1, 2, 3 . . . 12 . . . , in a computerized database.

Table 1 depicts the step 1 database relationship of various diseases (denoted A, B, C . . . with known indicators for the particular disease (denoted 1, 2, 3 . . . 12). It is seen that various ones of the indicators in increased (I), normal (N) or decreased (D) levels are associated with various ones of the diseases.

TABLE 1

| DISEASE (A, B, C, . . . ) | INDICATORS (1, 2, 3, 4, 5, 6, 7, 8, 9, 10, 11, 12, . . . ) |
|---|---|
| A | 1I, 2D, 7D, 9I, 10I |
| B | 1D, 3D, 6D, 8D, 10I, 12I |
| C | 2I, 3D, 5D, 7I, 10D |
| . | . |
| . | . |
| . | . |

By way of specific example, Table 2 describes three specific diseases, acute myocardial infarction, acquired hemolytic anemia and acromegaly, with related indicators. There are, of course, many diseases and several significant indicators for each, and medical research daily discovers, new diseases and derives new indicators for particular diseases. Thus, step 1 actually comprises a tabulation of known medical research of diseases and the indicator levels indicative of those diseases.

TABLE 2

| | Indicators |
|---|---|
| ACUTE MYOCARDIAL INFARCTION | |
| Increased levels: | Alkaline Phosphatase, Cholesterol, Creatinine, GGT, LDH, WBC, Neutrophils, Triglycerides, BUN, Uric Acid |
| Normal levels: | Total Bilirubin, Calcium |
| Decreased levels: | Albumin, Iron, Sodium |
| ACQUIRED HEMOLYTIC ANEMIA (AUTOIMMUNE) | |
| Increased levels: | SGOT, SGPT, Basophils, Total Bilirubin, Creatinine, LDH, Monocytes, Phosphorus, BUN, Uric Acid |
| Normal levels: | none |
| Decreased levels: | Hematocrit, Hemoglobin |
| ACROMEGALY | |
| Increased levels: | Alkaline Phosphatase, Calcium, Creatinine, Glucose, Phosphorous, Potassium, Sodium, BUN |
| Normal levels: | none |
| Decreased levels: | none |

As depicted in FIG. 1, step 2 of the method of the present invention is the creation of a second database which comprises a correlation of human diagnostic experience with each of the many indicators that are identified in the database of step 1. In the preferred embodiment, the database of step 2 includes a low value, a high value and a mean value for each of the indicators.

Table 3 represents the database of step 2, comprising the human experience values related to each of the indicators (1–12). Thus, the range of human experience for indicator 1 reveals a low of 0.9 units, a high of 2 units and a mathematical mean of 1.45 units.

TABLE 3

| INDICATOR | LOW | HIGH | MEAN |
|---|---|---|---|
| 1 | .9 | 2 | 1.45 |
| 2 | 3.5 | 5 | 4.25 |
| 3 | 60 | 415 | 237.5 |
| 4 | 4 | 14 | 9 |
| 5 | 0 | 3 | 1.5 |
| 6 | 0 | 200 | 100 |
| 7 | .2 | 1.3 | .75 |
| 8 | 8 | 20 | 14 |
| 9 | 6 | 25 | 15.5 |
| 10 | 8.8 | 10.1 | 9.45 |
| 11 | 1.3 | 3.3 | 2.3 |
| 12 | 95 | 105 | 100 |
| . | . | . | . |
| . | . | . | . |
| . | . | . | . |

Table 4 presents a typical tabulation of some known indicators with test results to provide added understanding by way of specific example. These test results and human experience high, low and mean are derived from known in medical research, and step 2 thus comprises a database of known medical research.

TABLE 4

| INDICATOR | RESULT | LOW | HIGH | MEAN | % STATUS | PRESENCE LEVEL |
|---|---|---|---|---|---|---|
| 1. A/G Ratio | 1.71 | 0.9 | 2 | 1.45 | 23.48 | N |
| 2. Albumin | 4.1 | 3.5 | 5 | 4.25 | −10.00 | N |
| 3. Alkaline Phosphatase | 114 | 60 | 415 | 237.5 | −34.79 | D |
| 4. Anion Gap | 16.2 | 4 | 14 | 9 | 72.00 | I |
| 5. Basophils | 0 | 0 | 3 | 1.5 | −50.00 | D |
| 6. Basophil Count | 0 | 0 | 200 | 100 | −50.00 | D |
| 7. Bilirubin, Total | 0.5 | 0.2 | 1.3 | 0.75 | −22.73 | N |
| 8. B.U.N. | 9 | 8 | 20 | 14 | −41.67 | D |
| 9. B.U.N./Creatinine Ratio | 18.00 | 6 | 25 | 15.5 | 13.16 | N |
| 10. Calcium | 9.77 | 8.8 | 10.1 | 9.45 | 19.23 | N |
| 11. Calcium/Phosphorus Ratio | 2.69 | 1.3 | 3.3 | 2.3 | 19.72 | N |
| 12. Chloride | 105 | 95 | 105 | 100 | 50.00 | I |
| . | . | . | . | . | . | . |

TABLE 4-continued

| INDICATOR | RESULT | LOW | HIGH | MEAN | % STATUS | PRESENCE LEVEL |
|---|---|---|---|---|---|---|
| . | | . | . | . | . | . |
| . | | . | . | . | . | . |

Returning to FIG. 1, step 3 of the method of the present invention is the development of test results for a specific individual. In the present invention, the individual test results are determined from testing blood, serum, urine or other bodily fluids through medical laboratory facilities. The results are correlated in a third database which includes the appropriate numerical values for each of the various indicators found in the databases of steps 1 and 2 hereabove. Table 5 is a simple test result tabulation for a specific individual as regards each of the indicators (1–12). These test results are the common output of a blood test, urine test, etc. with regard to the known indicators. For further understanding, these test results are also presented in Table 4.

TABLE 5

PATIENT TEST RESULTS

| INDICATOR | 1 | 2 | 3 | 4 | 5 | 6 | 7 | 8 | 9 | 10 | 11 | 12 |
|---|---|---|---|---|---|---|---|---|---|---|---|---|
| RESULT | 1.71 | 4.1 | 114 | 16.2 | 0 | 0 | .5 | 9 | 18 | 9.77 | 2.69 | 105 |

As depicted in FIG. 1, step 4 of the method of the present invention is the computerized comparison of the individual's indicator test results from the database developed in step 3 with the human experience database for the indicators developed in step 2. The comparison of step 4 is conducted utilizing the equation:

$$\% \text{ Status} = \frac{\text{Result} - \text{Mean}}{\text{Range (High-Low)}}$$

This comparison yields a result denoted as "percent status", which is a mathematical value which expresses a comparison of the individual's test results for a specific indicator with the typical human experience test result values for that particular indicator. It is an indication of where the individual's test results fall in comparison with the human experience test results of Table 3. Table 6 represents the step 4 comparison of the individual test results of Table 5 with the indicator statistics of Table 3 to derive a "percent status" according to the comparison equation presented above. For further understanding, the comparison results of step 4 (% status) are also presented in Table 4.

As depicted in FIG. 1, step 5 of the method of the present invention is the further analysis of the results of step 4 to determine the degree of presence of the various indicators in the specific individual's test results. In the present invention, where the percent status is greater than 25%, it is determined that an "increased level" (I) of that indicator is present. Where the percent status value of an indicator is less than −25%, it is determined that a "decreased level" (D) of that indicator is present. Where the percent status of an indicator is between −25% and +25%, it is determined that a "normal level" (N) of that indicator is present in the individual's test results. Table 6 includes the results of step 5, wherein an "I" represents an increased level presence, an "N" represents a normal level presence and a "D" indicates a decreased level presence of the various indicators. For further understanding, the presence indicator results of step 5 (I, N or D) are also presented in Table 4.

As depicted in FIG. 1, step 6 of the method of the present invention is the comparison of the indicator presence results of step 5 with the database of step 1. This correlation seeks to determine from the presence levels of various indicators in the individual's test results (I, N or D), the likelihood that particular diseases identified by the presence of specific combinations of indicators are afflicting the individual. This likelihood is derived by determining how many "pattern matches" exist between the presence levels (I, N or D) of the indicator test results with the indicator data of the step 1 database.

TABLE 7

| | DISEASE INDICATOR | | |
|---|---|---|---|
| DISEASE | # INDICATORS | # MATCHES | % MATCH |
| A | 5 | 0 | 0% |
| B | 6 | 4 | 67% |
| C | 5 | 2 | 40% |

TABLE 6

PRESENCE OF THE INDICATOR

| INDICATOR | 1 | 2 | 3 | 4 | 5 | 6 | 7 | 8 | 9 | 10 | 11 | 12 |
|---|---|---|---|---|---|---|---|---|---|---|---|---|
| % STATUS | 23.4 | −10 | −34 | 72 | −50 | −50 | −22 | −41 | 13 | 19 | 19 | 50 |
| PRESENCE LEVEL | N | N | D | I | D | D | N | D | N | N | N | I |

TABLE 7-continued

| DISEASE | # INDICATORS | # MATCHES | % MATCH |
|---------|--------------|-----------|---------|
| . | . | . | . |
| . | . | . | . |
| . | . | . | . |

For instance, as depicted in Table 7, the presence levels (I, N or D) of the various indicators are compared with various diseases A, B, C, . . . from the step 1 database as shown in Table 1 to determine the degree to which any of the diseases are indicated by the matching of the presence levels of various indicators with the disease data. Thus, as set forth in Table 7, it is seen that disease B is very likely present because 4 of 6 of the indicator levels are matched, whereas diseases A and C are not as likely present because fewer of the indicators levels for these diseases are matched. Table 8 is merely exemplificative of a portion of a typical result tabulation that is similar to Table 7 for added understanding.

TABLE 8

| DISEASE | ICD-9 CODE | # OF MATCHES | # OF INDICATORS | PERCENT MATCH |
|---------|-----------|--------------|-----------------|---------------|
| Anterior Pituitary Hypofunction | 253.40 | 5 | 10 | 50.00% |
| Pernicious Anemia | 281.00 | 6 | 15 | 40.00% |
| Vitamin C Deficiency | 267.00 | 3 | 8 | 37.50% |
| Rheumatoid Arthritis | 714.00 | 5 | 15 | 33.33% |
| Acute Myocardial Infarction | 410.00 | 5 | 15 | 33.33% |
| . | . | . | . | . |
| . | . | . | . | . |
| . | . | . | . | . |

Therefore, the basic method presented in FIG. 1 herein enables a medical practitioner to input a patient's test results into a computerized system and have the system produce a listing of possible diseases that the patient may have based upon the variation between the individual's test results and the known human experience results for various indicators.

Figure 2:
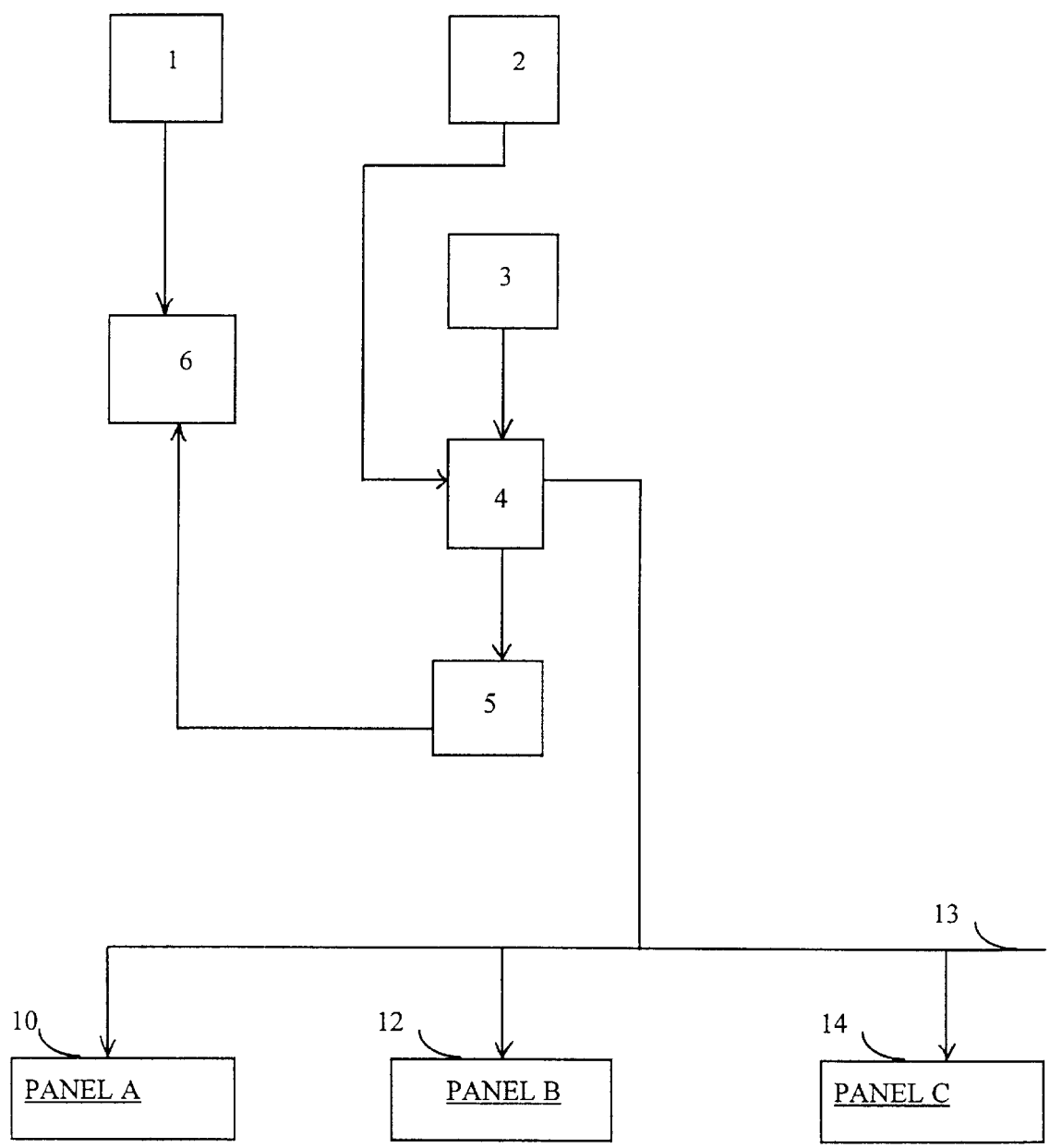
FIG. 2 is a block diagram showing the derivation of various panel status data results.

FIG. 2 depicts a further usage of the percent status data that was developed in step 4 of the basic method depicted in FIG. 1, and described above. It is well known in medical research that various ones of the specific indicators, denoted generally as 1, 2, 3 . . . 12 . . . are useful for the analysis of certain bodily conditions and functions, and a database which references a particular condition or function is referred to herein as a panel. Table 9 presents hypothetical data for three panels (Panel A, Panel B and Panel C) of many contemplated panels.

TABLE 9

| Panel A | | Panel B | | Panel C | |
|---------|---------|---------|---------|---------|---------|
| Indicator | % Status | Indicator | % Status | Indicator | % Status |
| 1 | 23.4 | 3 | -34. | 7 | -22. |
| 3 | -34. | 7 | -22 | 13 | 50. |
| 18 | 7.80 | 8 | -41 | 71 | -16.66 |
| 32 | -6.43 | 18 | 7.80 | | |
| | | 47 | -18.88 | | |
| | | 85 | 23.61 | | |

TABLE 9-continued

| Panel A | | Panel B | | Panel C | |
|---------|---------|---------|---------|---------|---------|
| Indicator | % Status | Indicator | % Status | Indicator | % Status |
| Deviation | 17.91 | Deviation | 24.55 | Deviation | 29.56 |
| Skew | -9.23 | Skew | -14.08 | Skew | 3.78 |

As depicted in FIG. 2 and shown in Table 9, panel A (see reference numeral 10) refers to a specific bodily condition or function, and information related to the panel A condition or function is obtainable from a combined analysis of indicators 1, 3, 18 and 32 (for example) wherein a percent status figure from step 4 is utilized for each indicator. A mathematical data deviation (the average of percent status without regard to the sign), and a data skew (the average of the percent status wherein the sign is taken into account), is calculated for each panel data set. The deviation and skew provide a numerical framework for referencing the status of the bodily condition or function of panel A. Also shown in Table 9 and depicted in FIG. 2 is a panel B (see reference numeral 12) which (for example) is represented by percent status data from indicators 3, 7, 8, 18, 47 and 85, with a deviation and skew being reported for panel B. Additionally, in Table 9 and in FIG. 2, a panel C (see reference panel 14) with indicators (for example 7, 12 and 71 with percent status data from step 4 and deviation and skew data) represents yet another bodily condition or function. Current medical knowledge teaches that many such bodily functions and conditions can be represented by data panels comprising a plurality of specific indicators, and while only panels A, B and C are shown in Table 9 and depicted in FIG. 2, arrow 13 is presented in FIG. 2 to indicate that many more such panels are contemplated by the inventor and considered part of the present invention.

Specific panels for bodily conditions and functions that are contemplated by the inventor include nitrogen status, electrolyte status, protein status, cardiac marker status, liver status, kidney function status, lipid status, allergy status, hematology status, leukocyte percentage differential status, blood element ratio status, leukocyte count status, acid PH indicator status, alkaline PH indicator status.

By way of specific examples to further the comprehension of the present invention, Table 10 hereof presents the electrolyte panel of an individual, the cardiac marker panel of the specific individual, the kidney function status panel of the individual and the blood elements ratio status panel of the individual.

TABLE 10

| INDICATOR | Result | % Status |
|---|---|---|
| ELECTROLYTE | | |
| Sodium | 139 | −10.00 |
| Potassium | 4.2 | −12.50 |
| Chloride | 105 | 50.00 |
| CO2 | 22 | −30.00 |
| Calcium | 9.7 | 19.23 |
| Phosphorus | 3.6 | −20.00 |
| Panel Status Deviation | | 23.62 |
| Panel Status Skew | | −0.54 |
| KIDNEY FUNCTION | | |
| B.U.N. | 9.0 | −41.67 |
| Phosphorus | 3.6 | −20.00 |
| Cholesterol | 181 | −17.21 |
| Creatinine | 0.5 | 0.00 |
| Uric Acid | 4.1 | 26.00 |
| Calcium | 9.7 | 19.23 |
| LDH | 414 | −31.95 |
| Total Protein | 6.5 | −30.00 |
| Albumin | 4.1 | −10.00 |
| Globulin | 2.4 | −60.00 |
| A/G Ratio | 1.7 | 23.48 |
| Panel Status Deviation | | 25.41 |
| Panel Status Skew | | −12.92 |
| RATIO'S | | |
| BUN/Creatinine | 18.00 | 13.16 |
| Sodium/Potassium | 33.10 | 9.13 |
| Calcium/Phosphorus | 2.69 | 19.72 |
| A/G Ratio | 1.71 | 23.48 |
| Anion Gap | 16.20 | 72.00 |
| Panel Status Deviation | | 27.50 |
| Panel Status Skew | | 27.50 |

TABLE 10-continued

| INDICATOR | Result | % Status |
|---|---|---|
| CARDIAC MARKER | | |
| Cholesterol | 181 | −17.21 |
| Triglycerides | 98.0 | 28.75 |
| SGOT | 23.0 | −5.00 |
| LDH | 414.0 | −31.95 |
| Panel Status Deviation | | 20.73 |
| Panel Status Skew | | −6.35 |

It is to be understood that other and further panels as identified above are within the contemplation of the inventor and will be known to those skilled in the art, and that medical research daily identifies other panels and further indicators that are suitable for usage in the various panels that may be derived utilizing the present invention.

Figure 3:
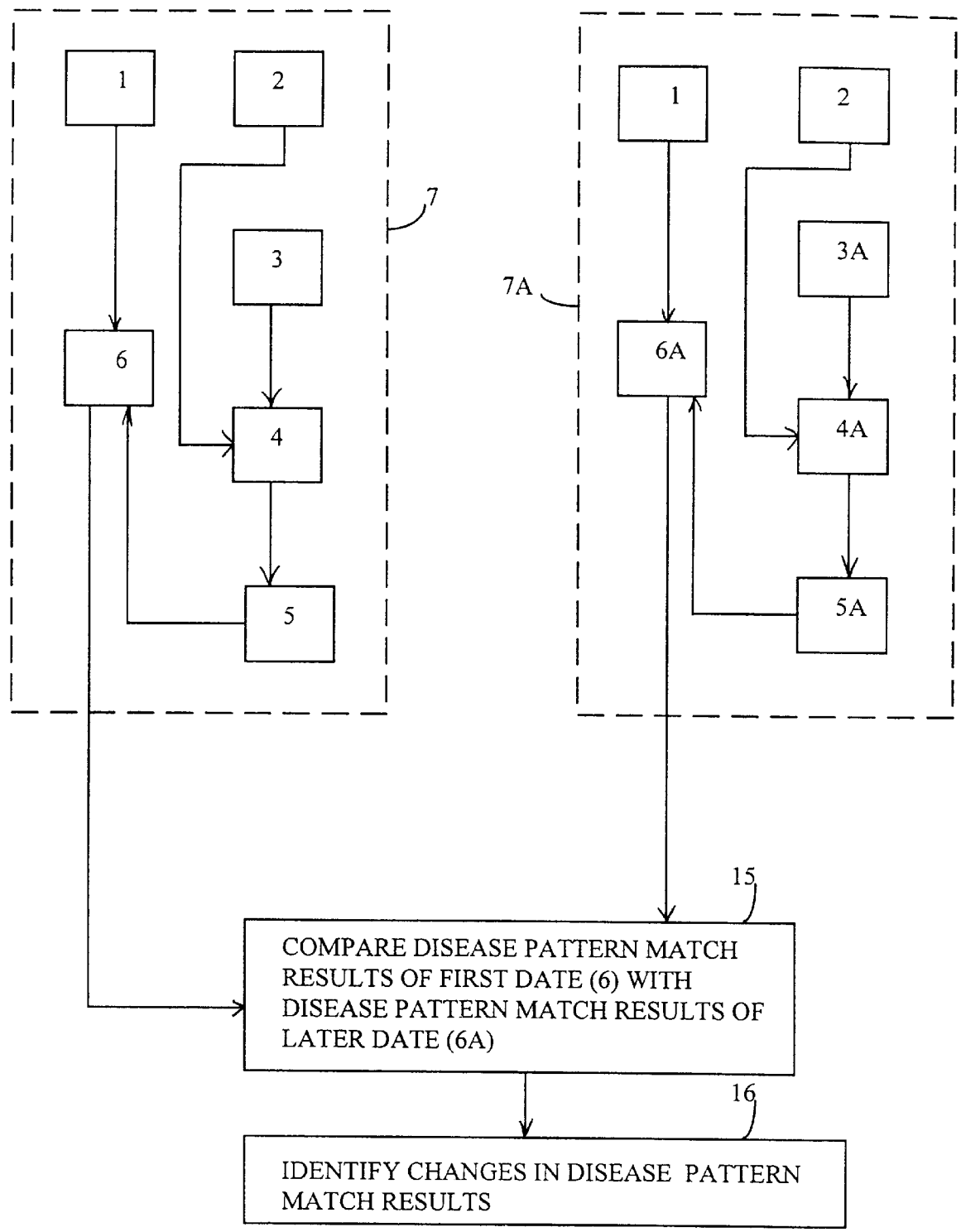
FIG. 3 is a block diagram showing the comparison of disease pattern match results of two separate dates.

The present invention contemplates the comparison of analytical test results data developed for an individual on a first date with test results data developed for the individual at a later date, in order to determine changes in the individual's medical condition. FIG. 3 is a schematic depiction of such a comparison, specifically a comparison of disease pattern match results and exemplificative data is provided in Table 11. As depicted in FIG. 3 and set forth in Table 11, a first set of disease pattern match data is derived from blood, urine or other fluid testing on a first date; this data is derived using portion 7 of the FIG. 3 schematic as discussed hereinabove with regard to FIG. 1 and shown in Table 8. On a second date (date A) further testing of the individual is accomplished, as represented by schematic portion 7A, wherein new personal bodily fluid test results 3A are developed. The test results 3A are compared with the human experience data 2 to yield new percent status data 4A for all indicators, which data 4A is utilized to develop in new presence levels 5A, and new disease pattern matches 6A as set forth in Table 11. The disease pattern match data of 6 and 6A is compared 15 and changes in disease pattern matches 16 are identified (see Table 11) as a means of providing health status data related to the individual.

TABLE 11

| DISEASE | ICD-9 CODE | # OF MATCHES (First Date) | # OF INDICATORS (First Date) | % MATCH (First Date) | # OF MATCHES (Date A) | % MATCH (Date A) | % CHANGE |
|---|---|---|---|---|---|---|---|
| Anterior Pituitary Hypofunction | 253.40 | 5 | 10 | 50.00 | 6 | 60.00 | −10.00 |
| Pernicious Anemia | 281.00 | 6 | 15 | 40.00 | 5 | 33.33 | +6.67 |
| Vitamin C Deficiency | 267.00 | 3 | 8 | 37.50 | 3 | 37.50 | 0 |
| Rheumatoid Arthritis | 714.00 | 5 | 15 | 33.33 | 5 | 37.50 | 0 |
| Acute Myocardial Infarction | 410.00 | 5 | 15 | 33.33 | 4 | 26.66 | +6.67 |
| . | . | . | . | . | . | . | . |
| . | . | . | . | . | . | . | . |
| . | . | . | . | . | . | . | . |

Figure 4:
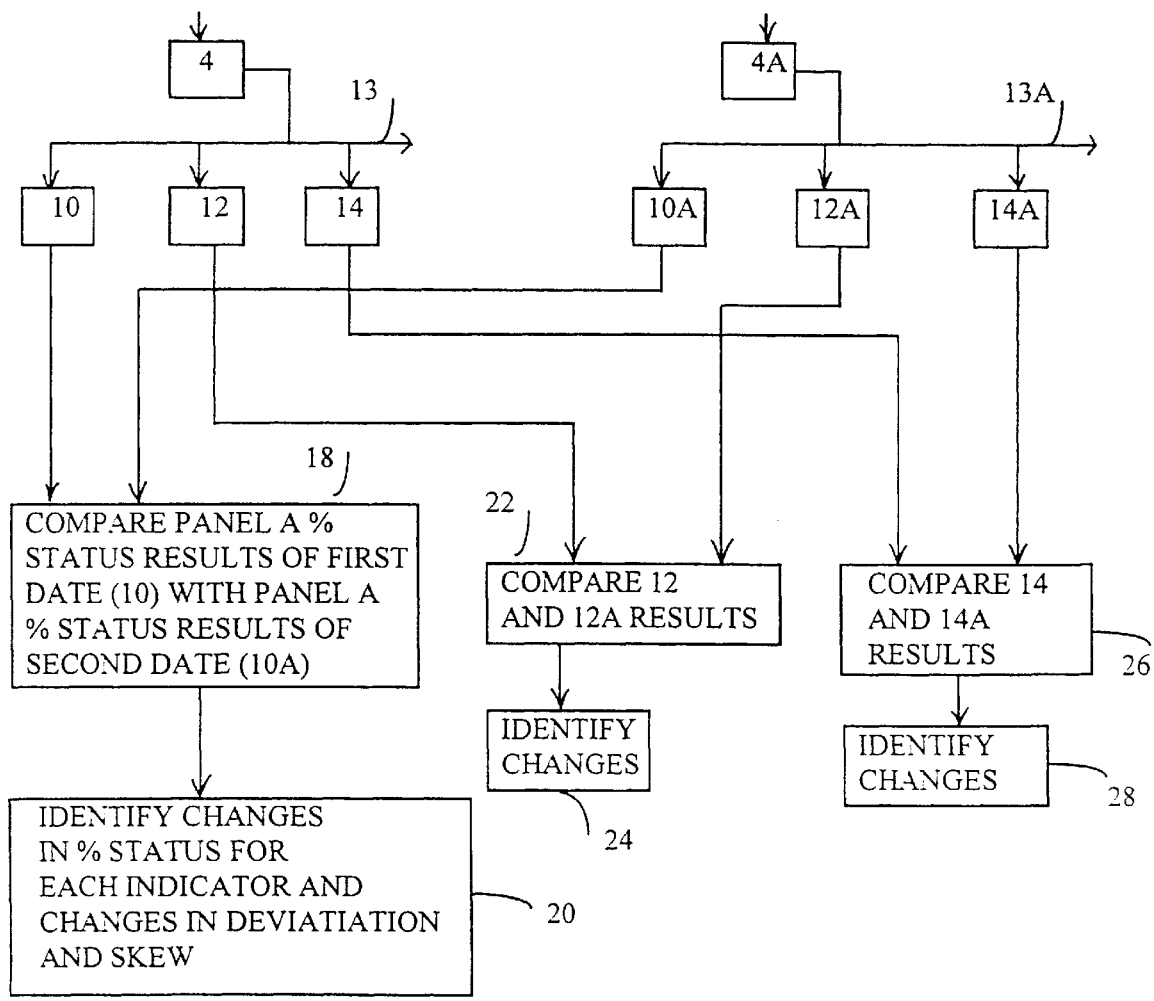
FIG. 4 is a block diagram depicting the comparison of panel status data for two separate dates.

The new percent status data developed for date A in step 4A of FIG. 3 can be utilized to develop new panel status information for date A in the same manner as is taught hereinabove with regard to FIG. 2. Thereafter, the panel status data of the first test date can be compared with the new panel status data for date A to provide information on the individual's medical health changes. FIG. 4 depicts such a panel status data comparison from a first date and a subsequent date A and Table 12 provides exemplificative data for panels A, B and C as discussed above in regard to Table 9.

TABLE 12

| Panel A Indicator | First Date % Status | Date A % Status | Comparison % Change |
|---|---|---|---|
| 1 | 23.4 | 25.0 | −1.6 |
| 3 | −34. | −28.0 | +6.0 |
| 18 | 7.80 | 7.8 | 0. |
| 32 | −6.43 | −6.43 | 0. |
| Deviation | 17.91 | | |
| Skew | −9.23 | | |

| Panel B Indicator | First Date % Status | Date A % Status | Comparison % Change |
|---|---|---|---|
| 8 | −34 | −28 | +6.0 |
| 7 | −22 | −22 | 0. |
| 8 | −41 | −45 | −4.0 |
| 18 | 7.80 | 7.8 | 0. |
| 47 | −18.88 | −20.0 | −1.12 |
| 85 | 23.61 | 23.61 | 0. |
| Deviation | 24.55 | | |
| Skew | −14.08 | | |

| Panel C Indicator | First Date % Status | Date A % Status | Comparison % Change |
|---|---|---|---|
| 7 | −22. | −22 | 0. |
| 13 | 50. | 42 | +8.0 |
| 71 | −16.66 | −8.4 | +8.26 |
| Deviation | 29.56 | | |
| Skew | 3.78 | | |

As depicted in FIG. 4, percent status data from step 4 of FIG. 3 at a first date is utilized to create panel status data 10, 12 and 14 as discussed above with regard to FIG. 2 and Table 9. In an identical manner on date A, percent status data derived in step 4A of FIG. 3 is utilized to create panel status data 10A, 12A and 14A as provided in Table 12. As mentioned above, further panels represented by arrows 13 and 13A are contemplated in the present invention. A comparison 18 of panel A percent status results of first date 10 with panel A percent status results of second date 10A is now accomplished as is shown in Table 12. The comparison 18 is utilized to identify changes 20 in the percent status for each indicator relevant to panel A, together with changes in the deviation and skew data. In a like manner, a comparison 22 of panel B status data 12 and 12A permits the identification 24 of changes in panel B medical status. Likewise, panel C status data is compared 26 to identify changes 28 in panel C medical status.

A specific example of the panel status data comparison is presented in Table 13 wherein the specific panels of Table 10 are utilized, those being the electrolyte panel, the cardiac marker panel, the kidney function status panel and the blood elements ratio status panel of a particular individual. As presented in Table 13, the panel results for the first date are reproduced from Table 10 and new panel results for date A are reported. It is furthermore indicated whether the change in specific indicators for each panel has improved (positive) or worsened (negative), and the change in the percent status of each indicator is reported. Additionally, the mathematical deviation and skew of the first date results and the date A results are provided and the change in the deviation and skew is also reported. The panel status data change of Table 13 is utilizable by a medical practitioner to provide insight into the medical health changes that the individual has undergone during the intervening period between the first date testing and the testing on date A.

TABLE 13

| | First Date | | Date A | Comparison | |
|---|---|---|---|---|---|
| INDICATOR | Result | % Status | % Results Status | Direction | % Change |
| ELECTROLYTE | | | | | |
| Sodium | 139 | −10.00 | −19.09 | Negative | −9.09 |
| Potassium | 4.2 | −12.50 | −17.50 | Negative | −5.00 |
| Chloride | 105 | 50.00 | −57.69 | Negative | −7.69 |
| CO2 | 22 | −30.00 | −42.50 | Negative | −12.50 |
| Calcium | 9.7 | 19.23 | 8.12 | Positive | 11.11 |
| Phosphorus | 3.6 | −20.00 | −26.67 | Negative | −6.67 |
| Panel Status Deviation | | 23.62 | 32.30 | | −8.68 |
| Panel Status Skew | | −0.54 | −5.51 | | −4.97 |
| KIDNEY FUNCTION | | | | | |
| B.U.N. | 9.0 | −41.67 | −57.05 | Negative | −15.38 |
| Phosphorus | 3.6 | −20.00 | −26.67 | Negative | −6.67 |
| Cholesterol | 181 | −17.21 | −4.64 | Positive | 12.57 |
| Creatinine | 0.5 | 0.00 | −14.29 | Negative | −14.29 |
| Uric Acid | 4.1 | 26.00 | 28.00 | Negative | −2.00 |
| Calcium | 9.7 | 19.23 | 8.12 | Positive | 11.11 |
| LDH | 414 | −31.95 | −45.90 | Negative | −13.95 |
| Total Protein | 6.5 | −30.00 | −38.00 | Negative | −8.00 |
| Albumin | 4.1 | −10.00 | 12.22 | Positive | 22.22 |
| Globulin | 2.4 | −60.00 | −50.48 | Positive | 9.52 |
| A/G Ratio | 1.7 | 23.48 | −4.61 | Positive | 28.09 |
| Panel Status Deviation | | 25.41 | 12.34 | | 13.07 |
| Panel Status Skew | | −12.92 | −10.81 | | 2.11 |
| RATIO'S | | | | | |
| BUN/Creatinine | 18.00 | 13.16 | 11.41 | Positive | 1.75 |
| Sodium/Potassium | 33.10 | 9.13 | 11.67 | Negative | −2.54 |
| Calcium/Phosphorus | 2.69 | 19.72 | 24.18 | Negative | −4.46 |
| A/G Ratio | 1.71 | 23.48 | −4.61 | Positive | 28.09 |
| Anion Gap | 16.20 | 72.00 | 71.00 | Positive | 1.00 |
| Panel Status Deviation | | 27.50 | 24.57 | | 2.93 |
| Panel Status Skew | | 27.50 | 22.43 | | 4.77 |
| CARDIAC MARKER | | | | | |
| Cholesterol | 181 | −17.21 | −29.78 | Positive | 12.57 |
| Triglycerides | 98.0 | 28.75 | 29.25 | Negative | −0.50 |
| SGOT | 23.0 | −5.00 | −7.38 | Negative | −2.38 |
| LDH | 414.0 | −31.95 | 45.90 | Negative | −13.95 |
| Panel Status Deviation | | 20.73 | 13.38 | | 7.35 |
| Panel Status Skew | | −6.35 | −7.42 | | −1.07 |

Figure 5:
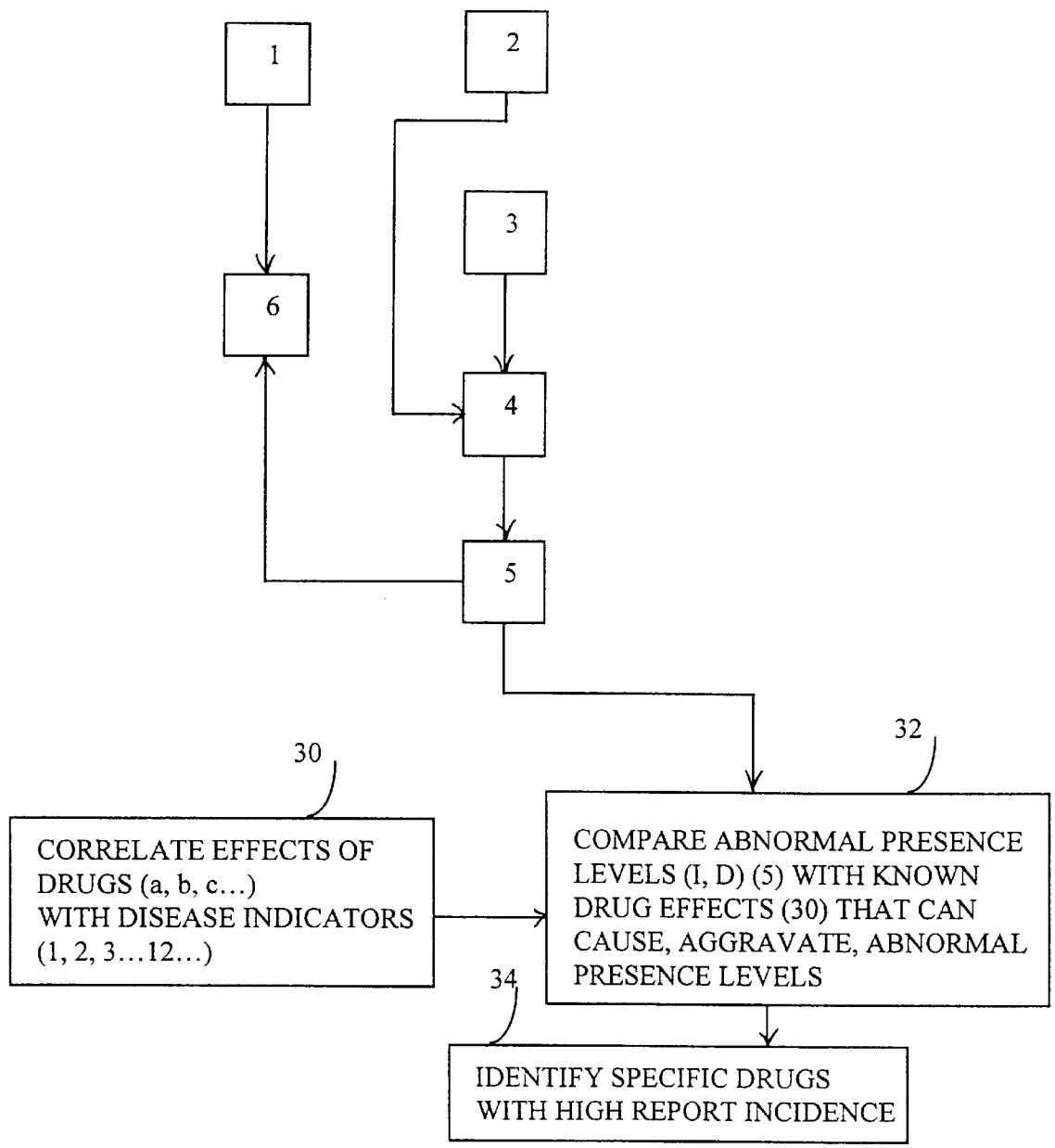
FIG. 5 is a block diagram showing the incorporation of known drug effect data with indicator status levels of the present invention.

A further feature of the present invention is the incorporation of the known effects of various drugs upon test results for various indicator levels. As depicted in FIG. 5, and set forth in exemplificative fashion in Table 14, a database is created 30 which correlates the effects of known drugs upon the levels of each of the various indicators. Thus, as depicted in Table 14, for each indicator 1, 2, 3 . . . 12 . . . known drugs are cataloged that can cause or aggravate an increased level (I) of an indicator and that can cause or aggravate a decreased level (D) of an indicator. The effects of the various drugs on the various indicator levels are well known in medical research and new drugs, and the corresponding effects thereof on various indicators are developed in medical research on a daily basis.

As shown in FIG. 5, the next step 32 in this analysis is to compare the abnormal presence levels, both increased (I) and decreased (D), determined in step 5 of the basic analytical process, with the drug effects table data of Table 14. By way of example, it is set forth hereabove in Table 6 that a specific individual's test results showed that indicators 1 and 2 showed a normal presence level, indicator 3 had a decreased presence level, indicator 4 had an increased presence level, indicators 5 and 6 had decreased presence levels.

TABLE 14

| INDICATOR | DRUG (a, b, c . . .) CAUSE OR AGGRAVATE | |
|---|---|---|
| | INCREASE (I) | DECREASE (D) |
| 1 | a, b, d, f, h | l, m, p |
| 2 | a, c, e, j, l | b, d, o, p |
| 3 | b, c, f, g | d, j, k, l, m |
| 4 | a, d, g, h | b, f, k |
| 5 | a, c, f, h, k, l | b, d, e, o, p |
| 6 | e, h, k, m | a, d, l, r, t |
| . | . | . |
| . | . | . |
| . | . | . |

Table 15 identifies the abnormal indicators 3, 4, 5 and 6, with their increased or decreased presence level, and identifies the specific drugs from Table 14 that cause or aggravate the increased or decreased presence level of the indicator.

TABLE 15

| INDICATOR | ABNORMAL PRESENCE LEVEL | DRUG CAUSE OR AGGRAVATE |
|---|---|---|
| 3 | D | d, j, k, l, m |
| 4 | I | a, d, g, h |
| 5 | D | b, d, e, o, p |
| 6 | D | a, d, l, r, t |
| . | . | . |
| . | . | . |
| . | . | . |
| HIGH INCIDENCE DRUG = d (CONTRAINDICATED) | | |

Thereafter, as set forth in step 34 of FIG. 5, the incidence of the various drugs set forth in Table 15 is determined. Specifically, it is seen in Table 15 that drug "d" is identified as a drug that can cause or aggravate each of the abnormal presence levels of each of the indicators. The analytical result of this analysis is the conclusion that drug "d" is contraindicated for this individual.

To further enhance the understanding of the present invention, Table 16 provides known drug effect medical research data for a few specific indicator conditions. Specifically, for the indicator chloride level in blood testing, where the chloride level is increased (% status is greater than 25%), some known drugs that can cause or aggravate this condition are listed; it is specifically noted that aspirin is one of these drugs. For the total iron level indicator, which is decreased (% status is less than –25%), some known drugs that can cause this reduced level are provided. For the basophils indicator decreased level (% status is less than –25%), a drug that can cause this reduced level is procainamide. For the WBC level indicator having a decreased level (% status is less than –25%), drugs that can cause this reduced level are listed, and it is specifically noted that aspirin is one of the drugs. For the glucose level indicator having a decreased level (% status is less than –25%), drugs which cause or aggravate the decreased level are identified, and it is specifically noted that aspirin is one such drug. The last indicator provided in Table 16 (it being understood that as many indicators as are identified in test results as having an increased or decreased level would be included in Table 16) is total protein having a decreased level (% status is less than –25%), and some of the various drugs that can cause or aggravate the reduced level are identified, specifically identifying aspirin as one of the drugs.

TABLE 16

| INDICATOR | ABNORMAL PRESENCE LEVEL | DRUG CAUSE OR AGGRAVATE CONDITION |
|---|---|---|
| Chloride | I | Acetazolamide, Aspirin, Lithium, Boric Acid . . . |
| Total Iron | D | ACTH, Oxalate, Fluorides . . . |
| Basophils | D | Procainamide, . . . |
| WBC | D | Aspirin, Busulfan, Mepazine . . . |
| Glucose | D | Aspirin, Ethanol, Insulin . . . |
| Total Protein | D | Aspirin, Arginine, Rifampin . . . |

An analysis of the Table 16 data shows that the drug aspirin is identified as a drug that can cause or aggravate four of the six abnormal presence levels of the indicators set forth therein; thus aspirin is a contraindicated drug for the individual whose test results are provided in Table 16.

It is therefore to be generally understood that the present invention includes a method as shown in FIG. 5 to identify specific drugs that are contraindicated for an individual based upon the increased or decreased levels of specific indicators in the individual's blood/fluid test analysis results. This output data of contraindicated drugs is obtained utilizing a database 30 correlating increased and decreased indicator levels with known drug effects from known medical research, and the specific indicators identified in step 5 test results as having increased or decreased levels pursuant to the analytical methods of the present invention.

Figure 6:
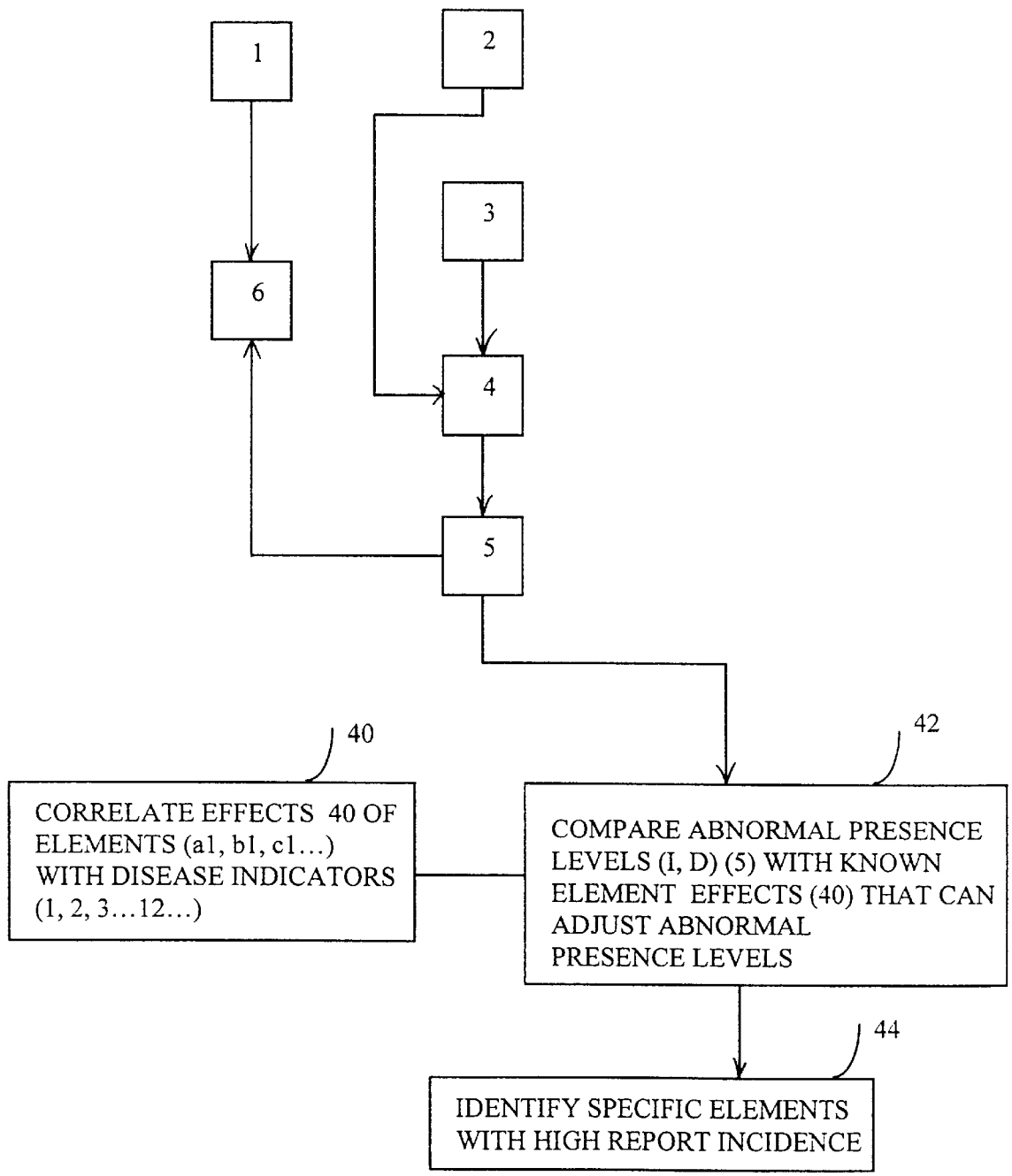
FIG. 6 is a block diagram showing the utilization of known effects of nutritional-biochemical elements with indicator levels.

Another feature of the present invention is the incorporation of the known positive effects of various pharmacological agents upon test results for various indicator levels. As depicted in FIG. 6, and set forth exempletive in Table 17, a database is created 40 which correlates the effects of known pharmacological agents (a1, b1, c1, . . . ) upon the levels for each of the various indicators. This table is similar to Table 14 with the significant difference that the effect of the pharmacological agents is to improve the abnormal presence level of various indicators.

TABLE 17

| INDICATOR | PHARMACOLOGICAL AGENT (a1, b1, c1 . . . ) EFFECT | |
|---|---|---|
| | INCREASE (I) | DECREASE (D) |
| 1 | b1, d1, f1, h1 | c1, k1, r1 |
| 2 | a1, g1, l1 | c1, l1, s1, t1 |
| 3 | d1, g1, h1, k1 | b1, c1, m1 |
| 4 | a1, k1, m1 | c1, d1, l1 |
| 5 | c1, k1, r1, s1 | a1, f1, g1, m1, p1 |
| 6 | a1, c1, n1, t1, v1 | d1, h1, k1, m1, s1 |
| . | . | . |
| . | . | . |
| . | . | . |

Thus, as depicted in Table 17, for each indicator 1, 2, 3 . . . 12 . . . known agents are cataloged that can normalize a level of an indicator; that is, to reduce an increased level or to raise a decreased level. The effects of the various pharmacological agents on the various indicator levels are well known in medical research, and new agents, and the corresponding effects thereof on various indicators are developed in medical research on a daily basis.

As shown in FIG. 6, the next step 42 in this analysis is to compare the abnormal presence levels, both increased (I) and decreased (D), determined in step 5 of the basic analytical process with the pharmacological agent data of Table 17. By way of example, it is set forth hereabove in Table 6 that a specific individual's test results showed that indicators 1 and 2 showed a normal presence level, indicator 3 had a decreased presence level, indicator 4 had an increased presence level, indicators 5 and 6 had decreased presence levels. Table 18 identifies the abnormal indicators 3, 4, 5 and 6 with their increased or decreased presence level, and identifies the specific pharmacological agents from Table 17 that can have a positive effect on the abnormal presence level indicated.

TABLE 18

| INDICATOR | ABNORMAL PRESENCE LEVEL | PHARMACOLOGY AGENT EFFECT |
|---|---|---|
| 3 | D | b1, c1, m1 |
| 4 | I | a1, k1, m1 |
| 5 | D | a1, f1, g1, m1, p1 |
| 6 | D | d1, h1, k1, m1, s1 |
| . | . | . |
| . | . | . |
| . | . | . |

HIGH INCIDENCE AGENT = m1 (INDICATED)

Thereafter, as set forth in step 44 of FIG. 6, the incidence of the various pharmacological agents set forth in Table 18 is determined. Specifically, it is seen in Table 18 that pharmacological agent m1 is identified as an agent that can have a positive effect on each of the abnormal presence levels of each of the indicators. The analytical result of this analysis is the conclusion that pharmacological agent m1 is positively indicated for this individual.

Figure 7:
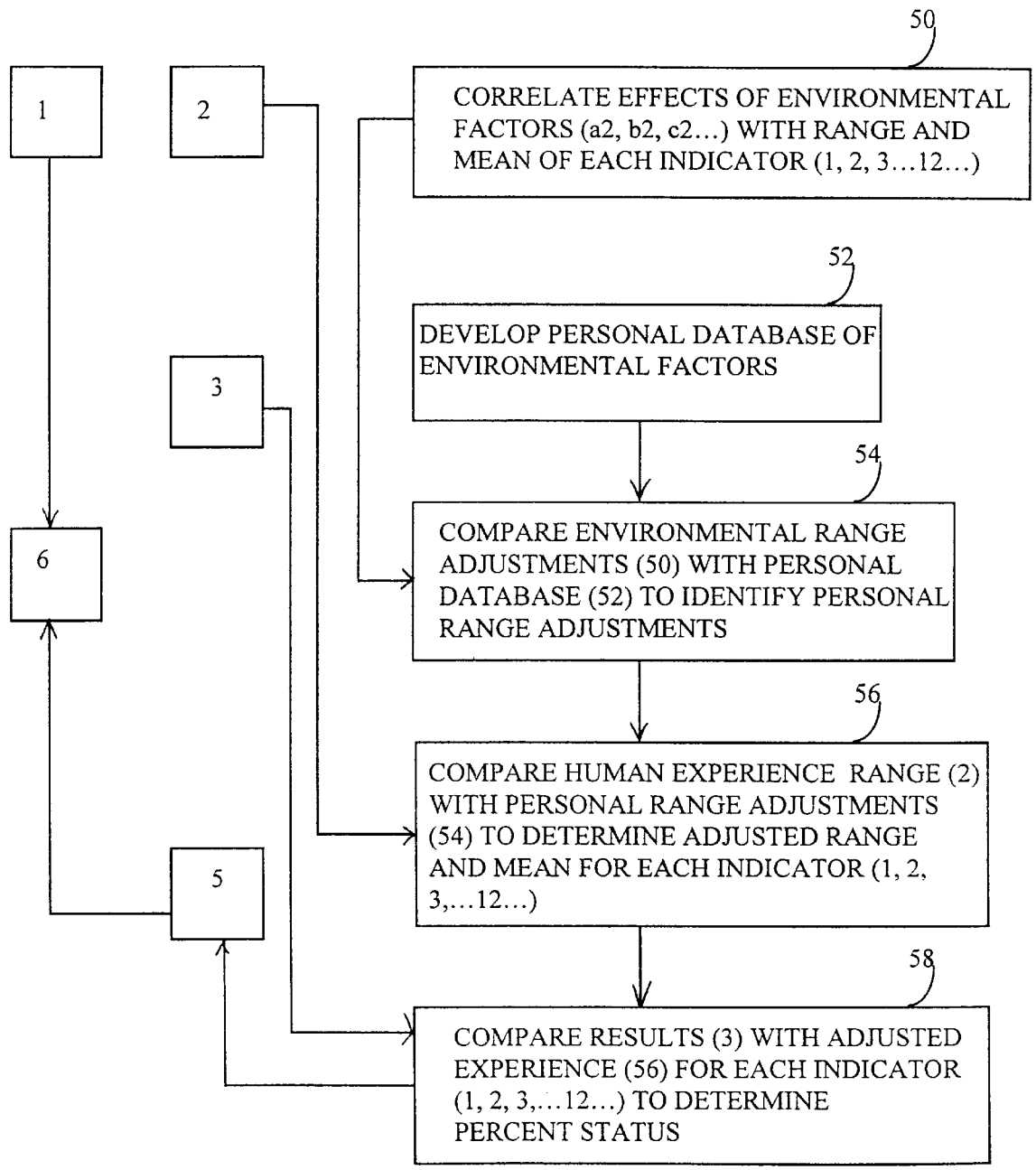
FIG. 7 is a block diagram showing the utilization of the known effects of various personal and/or environmental factors with the diagnostic system of the present invention.

It is well known in medical research that various environmental/personal factors can affect the indicator levels of an individual, or segments of the population generally. For example, such factors as age, sex, race, pregnancy, residence location, previous or current diseases, previous or current drug usage, etc., can all affect the various indicator levels. That is, a particular indicator level might be normal for a ten year old male and abnormal (increased or decreased) for a 65 year old female. FIG. 7 depicts the analytical steps of the present invention that incorporate the various environmental/personal factors.

As depicted in FIG. 7, a first step 50 in this portion of the analysis method of this invention is to create a database which correlates the effects of various environmental/personal factors (a2, b2, c2, . . . ) with the range and mean of each indicator (1, 2, 3 . . . 12 . . . ), and Table 19 is an example of such a database showing the effects of various factors, such as sex, pregnancy, altitude of residence and prior disease on the range (low and high) of various indicators, showing that some indicator ranges are affected by some of the factors whereas other indicator ranges are not.

TABLE 19

| | | | FACTORS (a2, b2, c2 . . . ) | | | | | | |
|---|---|---|---|---|---|---|---|---|---|
| | RANGE | | SEX | | PREGNANCY | | ALTITUDE | | PRIOR DISEASE |
| INDICATOR | LOW | HIGH | L | H | L | H | L | H | L | H |
| 1 | .9 | 2 | .6 | 1.5 | 1.2 | 4 | .4 | 1.0 | — | — |
| 2 | 3.5 | 5 | — | — | 5 | 10 | — | — | — | — |
| 3 | 60 | 415 | 80 | 600 | 30 | 300 | — | — | 30 | 400 |
| 4 | 4 | 14 | 5 | 18 | — | — | — | — | — | — |
| 5 | 0 | 3 | 0 | 2 | 0 | 6 | — | — | 0 | 6 |
| . | . | . | . | . | . | . | . | . | . | . |
| . | . | . | . | . | . | . | . | . | . | . |
| . | . | . | . | . | . | . | . | . | . | . |

The initial range results from Table 3 are presented for illustrative purposes.

Thereafter, as depicted in FIG. 7, an individual database of environmental/personal factors is created 52. Such a database is presented by way of example in Table 20.

TABLE 20

INDIVIDUAL ENVIRONMENTAL/PERSONAL FACTORS

Age - 45,   Sex - M,   Residence - High Altitude,
Prior Disease - hypothyroid, current drugs - thyroxin, aspirin.

The data which comprises Table 20 is obtained through a detailed medical background investigation and questionnaire responses of the individual.

In the next step 54 of this analysis, the environmental factor database 50 and the individual database of environmental factors 52 are compared 54 to identify the range adjustments of the specific indicators that require modification based upon the particular individual's environmental/personal factors. Such a comparison 54 is presented in Table 21 wherein it is seen that no adjustment to the normal levels (low and high) for indicators 2 and 4 is required, whereas adjustments for indicator levels 1, 3 and 5 are required due to the existence and effect of particular environmental/personal factors (altitude and prior disease) for this individual.

TABLE 21

| | INDIVIDUAL FACTORS | | | |
|---|---|---|---|---|
| | ALTITUDE | | PRIOR DISEASE | |
| INDICATOR | L | H | L | H |
| 1 | .4 | 1.0 | — | — |
| 2 | — | — | — | — |
| 3 | — | — | 30 | 400 |
| 4 | — | — | — | — |
| 5 | — | — | 0 | 6 |
| . | . | . | . | . |
| . | . | . | . | . |
| . | . | . | . | . |

The next step 56 in this analysis is to compare the human experience range data from the database of step 2 (see Tables 3 and 4) to create an adjusted range and mean for each indicator 1, 2, 3 ... 12 ... ). The result of this step 56 is the creation of a complete indicator database, similar to Table 3, wherein the individual factors are incorporated therewithin. Table 22 presents such a combined database.

TABLE 22

| INDICATOR | LOW | HIGH | MEAN |
|---|---|---|---|
| 1 | .4 | 1.0 | .70 |
| 2 | 3.5 | 5 | 4.25 |
| 3 | 30 | 400 | 215 |
| 4 | 4 | 14 | 9. |
| 5 | 0 | 6 | 3. |
| . | . | . | . |
| . | . | . | . |
| . | . | . | . |

The next step 58 in the analysis is to compare the blood/fluid test results of the individual (as derived in step 3 of the basic analysis) with the adjusted indicator database (see Table 22 from step 56). This step 58 is substantially identical to step 4 of the basic analysis, with the single difference being the utilization of the adjusted indicator levels from step 56 (as shown in Table 22) in place of the database created in step 2 of the basic analytical method. The result of this step 58 is the creation of the % status level for each indicator. This % status level is derived utilizing the equation set forth in step 4 above:

$$\% \text{ Status} = \frac{\text{Result} - \text{Mean}}{\text{Range (High-Low)}}$$

As discussed hereabove with regard to the basic method, the % status level is a mathematical value which expresses a comparison of the individual's test results for a specific indicator with the database of expected values and ranges for that indicator. Thereafter, the % status data from step 58 is utilized to determine the indicator presence levels (I, N, D) in the identical matter described hereabove in step 5 with regard to the basic method. The indicator presence level data may then be utilized in any and all of the analytical methods described hereabove.

Figure 8:
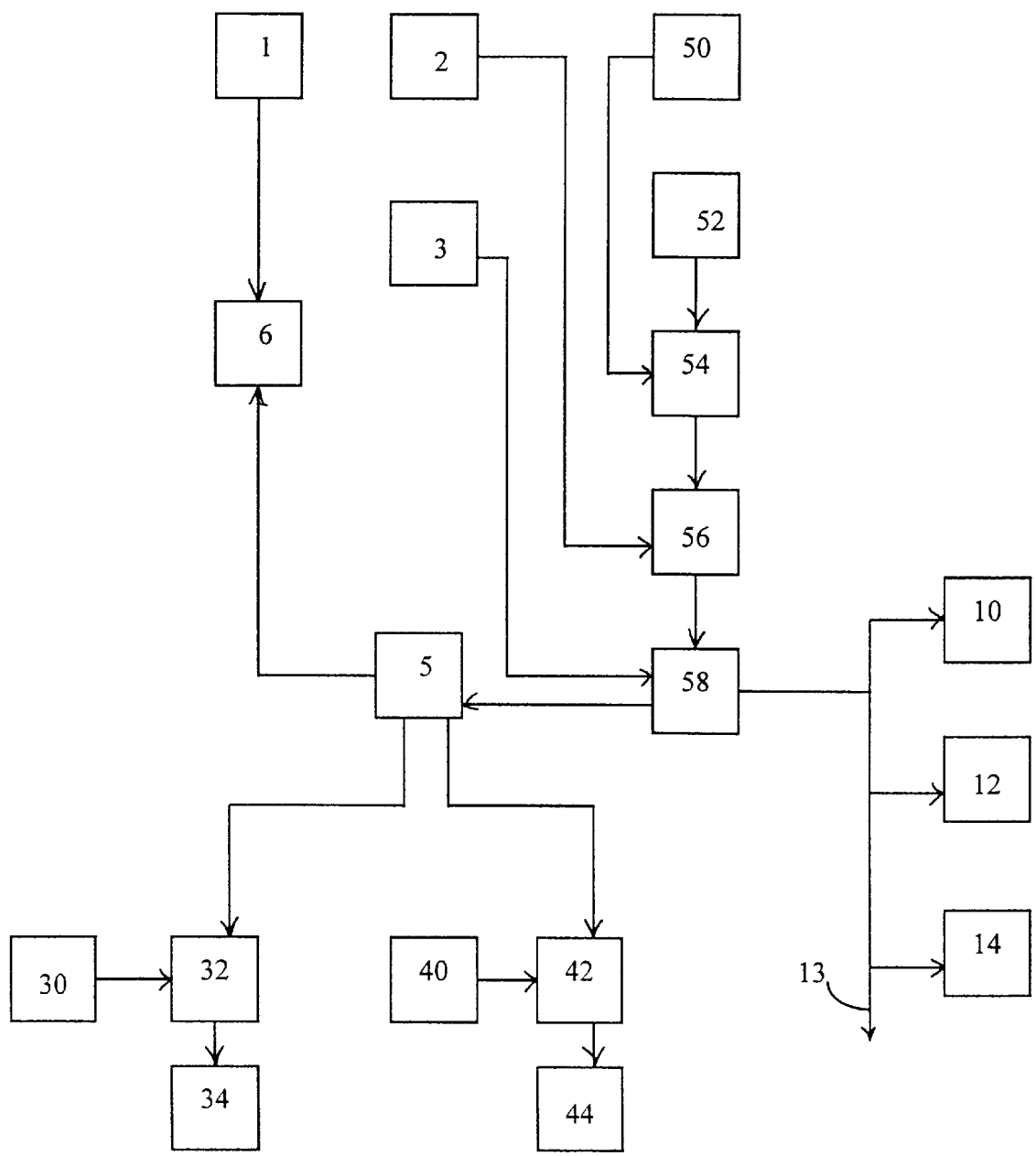
FIG. 8 is a block diagram showing the incorporation of the various analytical methods of FIGS. 2, 5, 6 and 7 with the basic diagnostic method of FIG. 1.

A comprehensive schematic diagram of the test method of the present invention is presented in FIG. 8. As depicted therein and discussed hereabove, the result of step 58 is the development of % status levels of all of the indicators based upon the individual's blood/fluid test results (step 3) and individualized indicator ranges (step 56). The % status levels from step 58 may then be utilized in creating panels 10, 12, 14. Additionally, the % status levels from step 58 are utilized in step 5 to identify presence levels of the indicators (decreased, normal and increased). The presence levels may then be utilized in a disease pattern match analysis in step 6, and/or they may be utilized in a drug effect analysis in steps 30, 32 and 34, and/or a pharmacological agent analysis in steps 40, 42 and 44, all as have been discussed hereabove.

Figure 9:
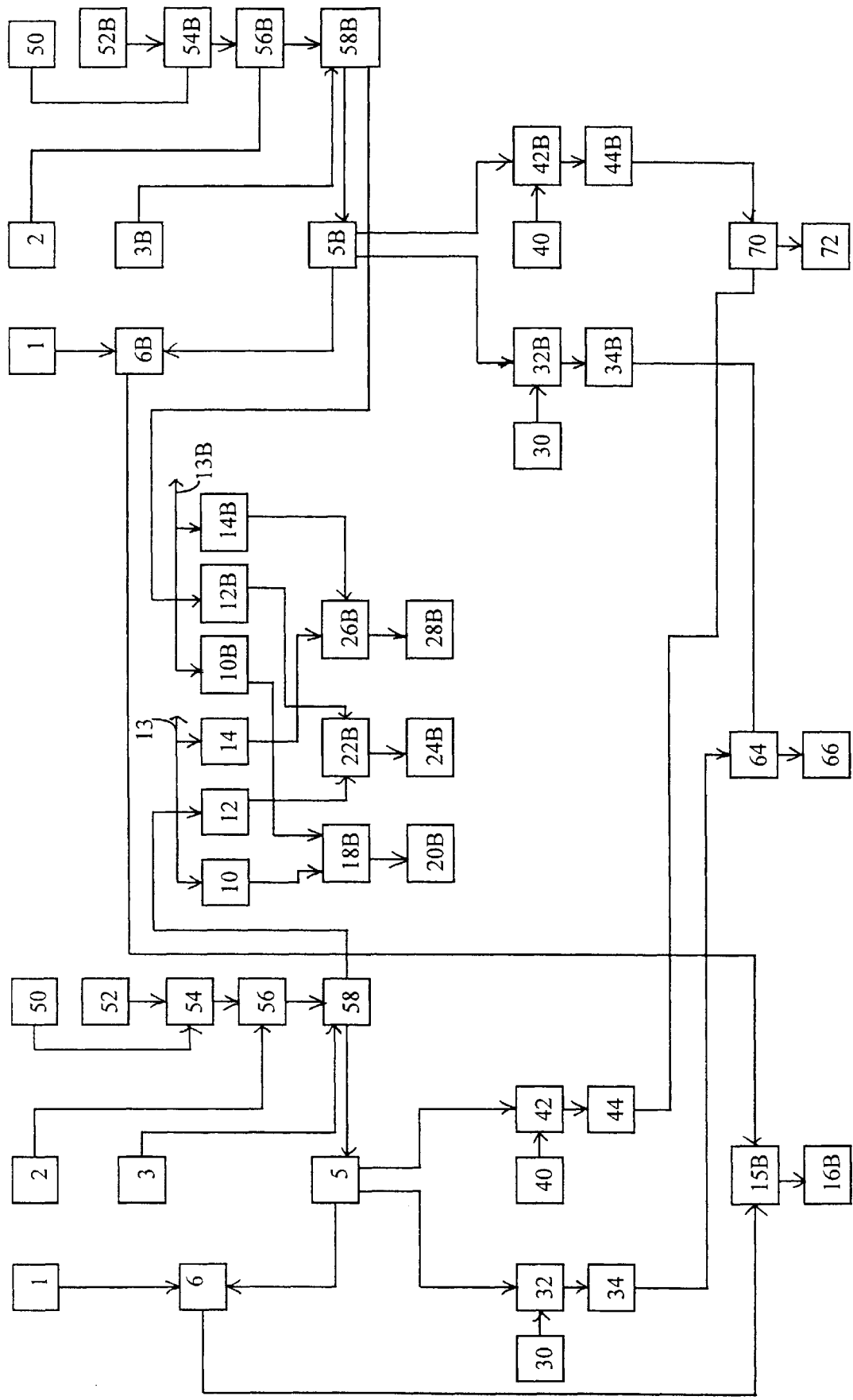
FIG. 9 is a block diagram showing the analytical method depicted in FIG. 8 utilizing individual test data from two separate dates and including data comparisons from those dates, including those shown in FIGS. 3 and 4.

FIG. 9 is a schematic diagram depicting the analysis method of FIG. 8 utilized on two different dates (first date and date B) to develop comparative medical results. The development of such comparative results is discussed hereabove with regard to FIGS. 3 and 4. It is therefore to be understood that on a first date a full analysis is conducted to provide disease pattern match data 6, panel data 10, 12, 14, drug interaction data 34 and pharmacological agent output data 44. Thereafter, on date B, further disease pattern match data 6B, panel data 10B, 12B and 14B, drug interaction data 34B and pharmacological agent output data 44B are created. The corresponding data from the two dates (first date and date b) may then be compared to provide comparative medical data reflective of the individual's medical health changes. Thus, the disease pattern match data 6 and 6B may be compared 15B to provide results indicative of changed disease pattern matches.

Similarly, panel data 10 and 10B, 12 and 12B, 14 and 14B may be compared, 18B, 22B and 26B respectively, to yield medical results 20B, 24B and 28B respectively indicating changes in panel results. Additionally, drug interaction results 34 and 34B may be compared 64 to provide data regarding changes in drug interactions that have occurred in the intervening time period between the first date and date B. Furthermore, the pharmacological agent data 44 and 44B may be compared 70 to yield data indicative of changes in pharmacological results during the time period.

It is therefore to be understood that the medical diagnostic analysis method of the present invention provides a comprehensive means for the utilization of individual blood/fluid test results, which may be combined with environmental/ personal factors related to a specific individual to yield significant medical data that is personalized and relevant to the individual's medical health.

While the present invention has been described with reference to certain preferred embodiments, it is to be understood that the present invention is not to be limited to such specific embodiments. Rather, it is the inventor's intention that the invention be understood and construed in its broadest meaning as reflected by the following claims. Thus, these claims are to be understood as incorporating and not only the preferred embodiment described herein but all those other and further alterations and modifications as would be apparent to those of ordinary skill in the art.

What I claim is:

1. A medical diagnostic method utilizing a computerized system having a means for data storage and a means for data processing, comprising:

a. storing a first database in said means for data storage, said first database having indicator data including human experience test result levels associated with each of a plurality of indicators;

b. storing a second database in said means for data storage, said second database having indicator data including a plurality of drugs and a plurality of indicators that are associated with each said drug;

c. inputting test results for an individual into said means for data processing, said test results including specific indicator levels associated with said individual;

d. determining an indicator presence level for each said indicator by comparing said specific indicator levels with said indicator data of said first database utilizing said means for data processing;

e. comparing said indicator presence levels with said indicator data of said second database utilizing said means for data processing, and providing a determination related to the effect of particular ones of said drugs in said individual.

2. A method as described in claim 1, wherein said indicator data of said second database includes a correlation of said drugs with increased and decreased levels of said indicators.

3. A method as described in claim 1, wherein said step of determining an indicator presence level includes the further step of determining whether said indicator presence level is increased or decreased.

4. A method as described in claim 1, wherein said indicator data of said first database includes a correlation of high, low and mean human experience test results for said indicators.

5. A method as described in claim 4, wherein said step of determining an indicator presence level includes the further step of determining a percent status value for each said indicator, said percent status value being determined from the relationship:

$$\% \text{ Status} = \frac{\text{Test Result} - \text{Mean}}{\text{Range (High-Low)}}.$$

6. A method as described in claim 5, wherein said step of determining an indicator presence level includes the further step of determining whether said percent status value is greater than 25% or less than −25%.

7. A method as described in claim 1, wherein said determination related to the effect of particular ones of said drugs in said individual includes a determination of drugs that cause or aggravate said indicator presence levels.

8. A method as described in claim 7, further including the step of:
   f. determining those drugs that are most commonly identified as causing or aggravating said indicator presence levels.

9. A method as described in claim 1, wherein steps a–e are performed on two different dates utilizing individual test results created on said two different dates to produce a said determination on each of said two different dates; and
   comparing said determinations from said two different dates to identify changes in said determinations.

10. A medical diagnostic method utilizing a computerized system having a means for data storage and a means for data processing, comprising:
    a. storing a first database in said means for data storage; said first database having indicator data including human experience test result levels associated with each of a plurality of indicators;
    b. storing a second database in said means for data storage, said second database having indicator data including a plurality of pharmacological agents and a plurality of indicators that are associated with each said agent;
    c. inputting test results for an individual into said means for data processing, said test results including specific indicator levels associated with said individual;
    d. determining an indicator presence level for each said indicator by comparing said specific indicator levels with said indicator data of said first database utilizing said means for data processing;
    e. comparing said indicator presence levels with said indicator data of said second database utilizing said means for data processing, and providing a determination related to the effect of particular ones of said agents in said individual.

11. A method as described in claim 10, wherein said indicator data of said second database includes a correlation of said agents with increased and decreased levels of said indicators.

12. A method as described in claim 10, wherein said step of determining an indicator presence level includes the further step of determining whether said indicator presence level is increased or decreased.

13. A method as described in claim 10, wherein said indicator data of said first database includes a correlation of high, low and mean human experience test results for said indicators.

14. A method as described in claim 13, wherein said step of determining an indicator presence level includes the further step of determining a percent status value for each said indicator, said percent status value being determined from the relationship:

$$\% \text{ Status} = \frac{\text{Test Result} - \text{Mean}}{\text{Range (High-Low)}}.$$

15. A method as described in claim 14, wherein said step of determining an indicator presence level includes the further step of determining whether said percent status value is greater than 25% or less than −25%.

16. A method as described in claim 10, wherein said determination related to the effect of particular ones of said agent in said individual includes a determination of agents that normalize said indicator presence levels.

17. A method as described in claim 16, further including the step of:
    f. determining those agents that are most commonly identified as normalizing said indicator presence levels.

18. A method as described in claim 10, wherein steps a–e are performed on two different dates utilizing individual test results created on said two different dates to produce a said determination on each of said two different dates; and
    comparing said determinations from said two different dates to identify changes in said determinations.

19. A medical diagnostic method utilizing a computerized system having a means for data storage and a means for data processing, comprising:
    a. storing a first database in said means for data storage, said first database having indicator data including human experience test result levels associated with each of a plurality of indicators, wherein said indicator data of said first database includes a correlation of high, low and mean human experience test results for each of said indicators;
    b. storing a second database in said means for data storage, said second database having indicator data including a plurality of drugs and a plurality of indicators that are associated with each said drug, wherein said indicator data of said second database includes a correlation of said drugs with increased and decreased levels of said indicators;
    c. inputting test results for an individual into said means for data processing, said test results including specific indicator levels associated with said individual;
    d. determining an indicator presence level for each said indicator by comparing said specific indicator levels with said indicator data of said first database utilizing said means for data processing, and wherein said step of determining an indicator presence level includes the further step of determining whether said indicator presence level is increased or decreased;
    e. comparing said indicator presence levels with said indicator data of said second database utilizing said means for data processing, and providing a determination related to the effect of particular ones of said drugs in said individual.

20. A method as described in claim 19, wherein said step of determining of an indicator presence level includes the further step of determining a percent status value for each said indicator, said percent status value being determined from the relationship:

$$\% \text{ Status} = \frac{\text{Test Result} - \text{Mean}}{\text{Range (High-Low)}}$$

and wherein said step of determining an indicator presence level includes the further step of determining whether said percent status value is greater than 25% as an indication that said indicator presence level is increased, or less than −25% as an indication that said indicator presence level is decreased.

21. A method as described in claim 20, wherein said determination related to the effect of particular ones of said drugs in said individual includes a determination of drugs that cause or aggravate said indicator presence levels.

22. A method as described in claim 21, wherein steps a–e are performed on two different dates utilizing individual test results created on said two different dates to produce a said determination on each of said two different dates; and comparing said determinations from said two different dates to identify changes in said determinations.

23. A method as described in claim 19, further including the step of:

f. determining those drugs that are most commonly identified as causing or aggravating said increased or decreased indicator presence levels.

24. A medical diagnostic method utilizing a computerized system having a means for data storage and a means for data processing, comprising:

a. storing a first database in said means for data storage; said first database having indicator data including human experience test result levels associated with each of a plurality of indicators, wherein said indicator data of said first database includes a correlation of high, low and mean human experience test results for each of said indicators;

b. storing a second database in said means for data storage, said second database having indicator data including a plurality of pharmacological agents and a plurality of indicators that are associated with each said agent, wherein said indicator data of said second database includes a correlation of said agents with increased and decreased levels of said indicators;

c. inputting test results for an individual into said means for data processing, said test results including specific indicator levels associated with said individual;

d. determining an indicator presence level for each said indicator by comparing said specific indicator levels with said indicator data of said first database utilizing said means for data processing, and wherein said step of determining an indicator presence level includes the further step of determining whether said indicator presence level is increased or decreased;

e. comparing said indicator presence levels with said indicator data of said second database utilizing said means for data processing, and providing a determination related to the effect of particular ones of said agents in said individual.

25. A method as described in claim 24, wherein said step of determining an indicator presence level includes the further step of determining a percent status value for each said indicator, said percent status value being determined from the relationship:

$$\% \text{ Status} = \frac{\text{Test Result} - \text{Mean}}{\text{Range (High-Low)}}$$

wherein said step of determining an indicator presence level includes the further step of determining whether said percent status value is greater than 25% as an indication that said indicator presence level is increased, or less than −25% as an indication that said indicator presence level is decreased.

26. A method as described in claim 25, wherein said determination related to the effect of particular ones of said agents in said individual includes a determination of agents that normalize said indicator presence levels.

27. A method as described in claim 26, wherein steps a–e are performed on two different dates utilizing individual test results created on said two different dates to produce a said determination on each of said two different dates; and comparing said determinations from said two different dates to identify changes in said determinations.

28. A method as described in claim 24, further including the step of:

f. determining those agents that are most commonly identified as normalizing said increased or decreased indicator presence levels.

29. In a medical diagnostic method utilizing a computerized system having a means for data storage and a means for data processing, including the steps of:

a. storing a first database in said means for data storage, said first database having indicator data including human experience test result levels associated with each of a plurality of indicators, wherein said indicator data of said first database includes a correlation of high, low and mean human experience test results for each of said indicators;

b. inputting test results for an individual into said means for data processing, said test results including specific indicator levels associated with said individual; the improvement therein comprising the steps of:

c. determining an indicator presence level for each said indicator by comparing said specific indicator levels with said indicator data of said first database utilizing said means for data processing, and wherein said step of determining an indicator presence level includes the further step of determining whether said indicator presence level is increased or decreased;

d. storing a second database in said means for data storage, said second database having indicator data including a plurality of drugs and a plurality of indicators that are associated with each said drug, wherein said indicator data of said second database includes a correlation of said drugs with increased and decreased levels of said indicators;

e. comparing said indicator presence levels with said indicator data of said second database utilizing said means for data processing, and providing a determination related to the effect of particular ones of said drugs in said individual.

30. In a method as described in claim 29, wherein said step of determining of an indicator presence level includes the further step of determining a percent status value for each said indicator, said percent status value being determined from the relationship:

$$\% \text{ Status} = \frac{\text{Test Result} - \text{Mean}}{\text{Range (High–Low)}}$$

the improvement therein comprising the further step of determining whether said percent status value is greater than 25% as an indication that said indicator presence level is increased, or less than −25% as an indication that said indicator presence level is decreased.

31. In a method as described in claim 30, wherein said determination related to the effect of particular ones of said drugs in said individual includes the improvement of a determination of drugs that cause or aggravate said indicator presence levels.

32. In a method as described in claim 31, wherein test results are obtained on two separate days and results are compared, the improvement therein comprising performing steps a–e on two different dates utilizing individual test results created on said two different dates to produce a said determination on each of said two different dates; and comparing said determinations from step (e) from said two different dates to identify changes in said determinations.

33. In a method as described in claim 29, the improvement therein comprising the further step of:

f. determining those drugs that are most commonly identified as causing or aggravating said increased or decreased indicator presence levels.

34. In a medical diagnostic method utilizing a computerized system having a means for data storage and a means for data processing, including the steps of:

a. storing a first database in said means for data storage; said first database having indicator data including human experience test result levels associated with each of a plurality of indicators, wherein said indicator data of said first database includes a correlation of high, low and mean human experience test results for each of said indicators;

b. inputting test results for an individual into said means for data processing, said test results including specific indicator levels associated with said individual; the improvement therein comprising the steps of:

c. determining an indicator presence level for each said indicator by comparing said specific indicator levels with said indicator data of said first database utilizing said means for data processing, and wherein said step of determining an indicator presence level includes the further step of determining whether said indicator presence level is increased or decreased;

d. storing a second database in said means for data storage, said second database having indicator data including a plurality of pharmacological agents and a plurality of indicators that are associated with each said agent, wherein said indicator data of said second database includes a correlation of said agents with increased and decreased levels of said indicators;

e. comparing said indicator presence levels with said indicator data of said second database utilizing said means for data processing, and providing a determination related to the effect of particular ones of said agents in said individual.

35. In a method as described in claim 34, wherein said step of determining an indicator presence level includes the further step of determining a percent status value for each said indicator, said percent status value being determined from the relationship:

$$\% \text{ Status} = \frac{\text{Test Result} - \text{Mean}}{\text{Range (High–Low)}}$$

the improvement therein comprising the further step of determining whether said percent status value is greater than 25% as an indication that said indicator presence level is increased, or less than −25% as an indication that said indicator presence level is decreased.

36. In a method as described in claim 35, wherein said determination related to the effect of particular ones of said agents in said individual includes the improvement of a determination of agents that normalize said indicator presence levels.

37. In a method as described in claim 36, wherein test results are obtained on two separate days and results are compared, the improvement therein comprising performing steps a–e on two different dates utilizing individual test results created on said two different dates to produce a said determination on each of said two different dates; and comparing said determinations from step (e) from said two different dates to identify changes in said determinations.

38. In a method as described in claim 34, the improvement therein comprising the further step of:

f. determining those agents that are most commonly identified as normalizing said increased or decreased indicator presence levels.

\* \* \* \* \*